(12) United States Patent
Villa et al.

(10) Patent No.: US 7,759,517 B2
(45) Date of Patent: Jul. 20, 2010

(54) PROCESS FOR THE PREPARATION OF GABAPENTIN

(75) Inventors: Marco Villa, Milan (IT); Maurizio Paiocchi, Milan (IT); Katiuscia Arrighi, Misinto (IT); Francesco Corcella, Parabiago (IT); Vincenzo Cannata, Sasso Marconi (IT); Giorgio Soriato, Caldiero (IT); Massimo Verzini, Caldiero (IT)

(73) Assignee: Zach System S.P.A., Bresso (IT)

( * ) Notice: Subject to any disclaimer, the term of this patent is extended or adjusted under 35 U.S.C. 154(b) by 879 days.

(21) Appl. No.: 11/571,192

(22) PCT Filed: Jun. 22, 2005

(86) PCT No.: PCT/EP2005/052906

§ 371 (c)(1),
(2), (4) Date: Dec. 22, 2006

(87) PCT Pub. No.: WO2006/000562

PCT Pub. Date: Jan. 5, 2006

(65) Prior Publication Data

US 2008/0097122 A1    Apr. 24, 2008

(30) Foreign Application Priority Data

Jun. 24, 2004    (IT)    .......................... MI2004A1271

(51) Int. Cl.
*C07C 61/08*    (2006.01)
(52) U.S. Cl. ..................... 562/507; 562/506; 562/400; 564/138; 564/123
(58) Field of Classification Search ................. None
See application file for complete search history.

(56) References Cited

U.S. PATENT DOCUMENTS

2004/0063997 A1* 4/2004 Ferrari et al. ............... 562/507

FOREIGN PATENT DOCUMENTS

| WO | 03/002504 | 1/2003 |
| WO | 03/002517 | 1/2003 |

* cited by examiner

*Primary Examiner*—Karl J Puttlitz
*Assistant Examiner*—Sudhakar Katakam
(74) *Attorney, Agent, or Firm*—Oblon, Spivak, McClelland, Maier & Neustadt, L.L.P.

(57) ABSTRACT

The present invention relates to a process for the preparation of gabapentin and, more in particular, to a method of synthesis of 1,1-cyclohexane acetic acid monoamide, an intermediate used in the preparation of gabapentin, comprising the basic hydrolysis reaction of α,⊣-diaminocarbonyl-β,β-pentamethylene glutarimide.

19 Claims, No Drawings and 5,091,567, both in the name of Goedecke A G.
PROCESS FOR THE PREPARATION OF GABAPENTIN The present invention relates to a process for the preparation of gabapentin and, more in particular, to a method of synthesis of 1,1-cyclohexane acetic acid monoamide, an intermediate used in the preparation of gabapentin.

Gabapentin, 1-(aminomethyl)-cyclohexane acetic acid (The Merck Index, XII ed., page 733, no. 4343) is a known drug with anti-epileptic activity, described the first time by Warner-Lambert Co. in U.S. Pat. No. 4,024,175.

In the literature, several processes for the preparation of gabapentin are reported; see for example the U.S. Pat. No. 4,024,175, previously mentioned, U.S. Pat. Nos. 5,068,413, and 5,091,567, both in the name of Goedecke A G.

The U.S. Pat. No. 4,024,175 describes various processes for the preparation of gabapentin or analogous compounds of formula

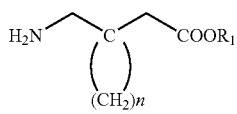

wherein $R_1$ is a hydrogen atom or a lower alkyl and n is 4, 5 or 6;
characterised by the use of conventional methods for the preparation of primary amines or amino acids such as, for example, the Curtius, Hoffmann and Lossen rearrangement.

In particular, the aforesaid patent in the name of Warner Lambert Co., example 4 variant A, column 5, describes the synthesis of the lower cyclic homologous derivative of gabapentin, 1-(methylamino)-1-cyclopentane acetic acid, through the preparation of cyclopentane diacetic acid monoamide, carried out by reaction of the corresponding anhydride with a 20% aqueous solution of $NH_3$, the Hofmann rearrangement of the monoamide thus obtained, acidification and extraction followed by a final purification step which consists in the elution through a basic ionic exchange resin and in re-crystallisation from alcohols.

Substantially, the processes for the preparation of 1,1-cyclohexane diacotic acid monoamide described in the literature provide for the synthesis of the corresponding acid and the subsequent conversion via anhydride according to conventional methods.

The synthetic scheme can be summarised as follows:

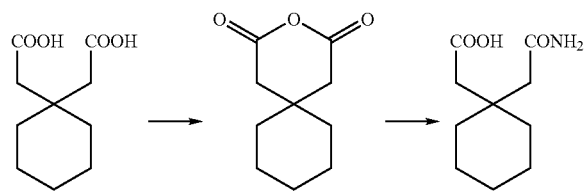

The international patent application WO 03/002517 in the name of Bromine Compounds describes a process for the synthesis of 1,1-cyclohexane diacetic acid monoamide which comprises the amination of the 1,1-cyclohexane diacetic acid anhydride with aqueous ammonia.

The patent CN 1297885 (Hangzhou Shouxin Fine Chem) describes the preparation of 1,1-cyclohexil oxalic acid monoamide through the reaction of the corresponding anhydride with aqueous or gaseous ammonia in the presence of an organic solvent.

Therefore, cyclohexane diacetic acid is a key substrate in the preparation of the monoamide and, hence, indirectly in the preparation of gabapentin end product.

1,1-cyclohexane diacetic acid is prepared according to known techniques which refer to literature articles from the start of the last century.

The synthetic scheme can be summarised as follows:

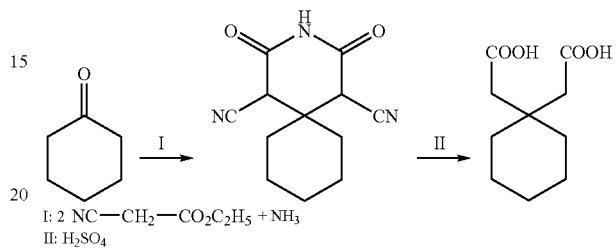

I: 2 NC—$CH_2$—$CO_2C_2H_5$ + $NH_3$
II: $H_2SO_4$

Thorpe, J. Chem. Soc. 1919, 115, 686-704, describes the synthesis of α,α'-dicyan-β, β-pentamethylene glutarimide (hereafter, "dinitryl") starting from cyclohexanone, ethyl cyanoacetate and ammonia in alcoholic solution.

Thorpe, J. Chem. Soc. 1911, 99, 445-446 describes the hydrolysis of intermediate dinitryl to 1,1-cyclohexane diacetic acid by dissolution in concentrated sulphuric acid.

The same synthetic scheme is described in A. I. Vogel, J. Chem. Soc. 1934, 1768-1765 and in the patents FR 1.248.764 in the name of Centre de Lyophilisation Pharmaceutique, GB 898.692 in the name of Warner-Lambert Pharmaceutical and in the aforementioned Chinese patent CN 1297885 (Hangzhou Shouxin Fine Chem).

The U.S. Pat. No. 6,613,904 describes a process for the preparation of the intermediate dinitryl compound which comprises the reaction of a ketone such as, for example, cyclohexanone with ethylcyanoacetate in the presence of ammonium hydroxide.

A recent international patent application WO 03/002504 describes a process for the preparation of 1,1-cyclohexane diacetic acid starting from 1,5-dicarbonitryl-2, 4-dioxo-3-azaspiro[5,5]-undecane (imide) by reaction with sulphuric acid in two steps at different temperature.

The U.S. Patent application US 2004/0063997 describes a process for the synthesis of gabapentin hydrochloride which comprises the reaction of a mixture of acetic anhydride/ammonium acetate with 1,1-cyclohexane diacetic acid to yield 3,3-pentamethylene-glutarimide, the treatment of said imide with sodium hydroxide until dissolution, the dripping of the solution thus obtained in a mixture of sodium hydroxide/sodium hypochlorite and acidification with hydrochloric acid.

Therefore, according to the literature, the preparation of 1,1-cyclohexane diacetic acid monoamide is subordinated to the isolation and to the conversion of the corresponding acid.

Consequently, it becomes necessary to study alternative methods which allow to prepare 1,1-cyclohexane diacetic acid monoamide with a reduced number of synthetic steps and, hence, under more favourable conditions from the viewpoint of the industrial application of the process.

We have now surprisingly found a method of synthesis of 1,1-cyclohexane diacetic acid monoamide, intermediate in the preparation of gabapentin at the industrial level, which allows to overcome the drawbacks of the processes described by the prior art.

Therefore, object of the present invention is a process for the preparation of 1,1-cyclohexane diacetic acid monoamide which comprises the basic hydrolysis reaction of α,α'-diaminocarbonyl-β,β-pentamethylene glutarimide.

The preparation of α,α'-diaminocarbonyl-β,β-pentamethylene glutarimide (hereafter, "diamide") is carried out by reaction of a solution of dinitryl with sulphuric acid at a temperature comprised between 65 and 85° C. as described in the aforementioned international patent application WO 03/002504.

In the aforesaid patent application, the diamide is described as an intermediate in the preparation of 1,1-cyclohexane diacetic acid, but it is neither isolated nor characterised, as proven by the fact that it has not been attributed a Registry Number by the Chemical Abstract Service.

Therefore, a further object of the present invention is the compound (α,α'-diaminocarbonyl-β, β-pentamethylene glutarimide in solid form.

In a preferred embodiment, the diamide is prepared through dinitryl hydrolysis with a sulphuric acid solution followed by neutralisation of the obtained solution and by precipitation of the product.

The hydrolysis reaction is generally carried out by adding dinitryl to an aqueous solution of sulphuric acid.

The dinitryl addition to the water/sulphuric acid solution is preferably carried out in portions.

Each portion is preferably added after solubilisation of the previous portion at a temperature around 60° C. in order to control the exothermy of the reaction.

The hydrolysis reaction is carried out at a temperature comprised between 25 and 70° C. and it is preferably carried out at a temperature between 50 and 60° C. Maintaining temperature below 70° C. and preferably around 50° C. in the phase that precedes neutralisation allows to minimise the formation of by-products.

The hydrolysis reaction of dinitryl takes place by reaction with sulphuric acid generally used in aqueous solution at a concentration comprised between 75% and 85% and preferably with sulphuric acid in aqueous solution at a concentration around 85%.

The molar ratio between sulphuric acid and dinitryl is generally comprised between 4.4 and 9.3 and preferably between 6.1 and 7.5 in order to optimise yield (on average around 90-95%) and limit scraps.

The neutralisation reaction is carried out with a water/sulphuric acid mixture, preferably in a weight ratio comprised between 0.65 and 1.8 and yet more preferably around 1, in order to optimise the reaction conditions promoting diamide precipitation.

To obtain an easily filterable product, it is preferable that the reaction mixture be added to the water used in neutralisation and not vice versa.

Moreover, said procedure allows better control on the thermal development of the reaction.

By this method, a highly pure product is obtained.

Therefore, a further object of the present invention is the compound α,α'-diaminocarbonyl-β, β-pentamethylene glutarimide in solid form with a purity higher than 95%.

The diamide basic hydrolysis reaction, object of the present invention, to yield the 1,1-cyclohexane diacetic acid monoamide is generally carried out by reaction with a solution of sodium hydroxide.

In a preferred embodiment, hydrolysis is carried out according to a method in which three distinct phases can be identified:

a) hydrolysis of α,α'-diaminocarbonyl-β,β-pentamethylene glutarimide to obtain α,α'-di-acid disodium salt;

b) decarboxylation to obtain pentamethylene-glutarimide;

c) hydrolysis of pentamethylene-glutarimide and precipitation of the product.

It is preferable to proceed according to this method in order to limit the formation of salts such as, for example, ammonium carbonate which could entail technical problems in the execution of the procedure.

The process thus takes place according to the following synthetic scheme, where only the main intermediates are shown:

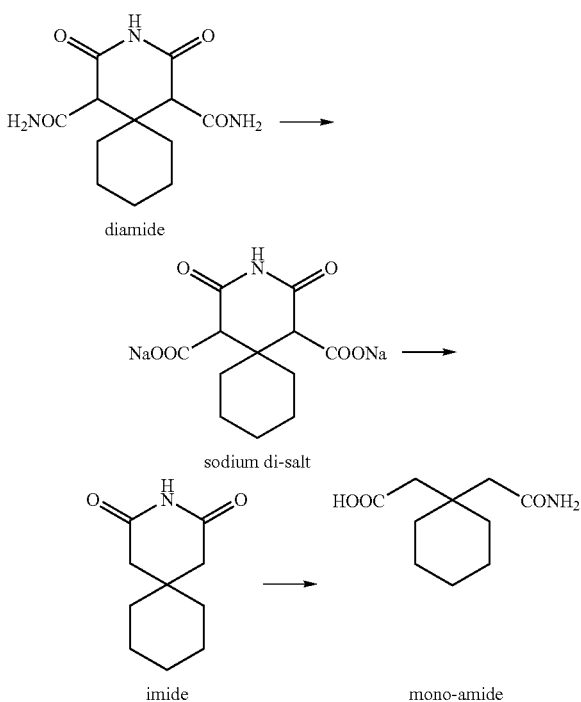

It is evident that the three steps identified by us are not procedurally binding.

The intermediates of the monoamide preparation process can be isolated or not, with the consequent reduction of the number of steps required to obtain the product.

The first step consists of diamide hydrolysis to yield the diacid disodium salt and it is carried out by addition of the dry diamide at low temperature in a sodium hydroxide solution, preferably with a concentration around 30%, and beating for a few hours at reflux at a temperature around 105-110° C.

The addition of diamide is preferably carried out at a temperature comprised between −5 and 5° C. for better control of the reaction, considering the massive release of gaseous ammonia.

Once heating is complete, one has the complete formation of the diacid disodium salt and the nearly complete elimination of ammonia which is released by the reaction itself.

The sodium hydroxide/diamide molar ratio is preferably comprised between 3.5 and 4, in light of its influence on reaction velocity.

The compound α,α'-aminocarbonyl-β,β-pentamethylene glutarimide di-sodium di-salt is new and constitutes a further object of the present invention.

The second step comprises the decarboxylation of the diacid disodium salt to yield the imide of the 1,1-cyclo hexane diacetic acid.

To optimise the decarboxylation step while keeping carbon dioxide development under control, the method is preferably carried out by addition of a solution formed by water and synthetic hydrochloric acid at a portion of about 15-20% by weight of the diacid disodium salt solution maintained at a temperature around 50° C. and heating the reaction mixture to about 95° C. The imide crystallises to yield a suspension and thereto is then added, in about one hour, the remaining solution of diacid disodium salt maintaining temperature around 95° C. At the end of the addition, the suspension is maintained at temperature until the reaction is complete. The third step comprises the hydrolysis of the imide and the precipitation of the reaction product, i.e. 1,1-cyclohexane diacetic acid monoamide, by acidification.

The hydrolysis reaction is carried out by adding sodium hydroxide preferably at a concentration comprised between 10 and 30% and bringing to reflux. The molar ratio between sodium hydroxide and diamide is preferably comprised between 3.8 and 4.7, considering the total moles used, and yet more preferably around a value of 4.3, in order to optimise the hydrolysis reaction and promote the subsequent precipitation of the product.

The precipitation is generally carried out by adding hydrochloric acid, preferably synthetic.

Preferably, the reaction is carried out in the presence of a precipitation co-solvent, e.g. isopropanol and ethyl acetate.

Yet more preferably, it is carried out in the presence of isopropanol.

To obtain a greater yield and productivity, an isopropanol/diamide weight ratio comprised between 0.5 and 1 is preferably used, and yet more preferably around 0.5.

The acidification of the reaction mixture is generally carried out until obtaining a pH comprised between 2 and 6 and yet more preferably around a value of 4.0-4.5.

The attainment of the optimal precipitation pH can be effected in two steps, e.g. by a first addition of acid until obtaining a pH around 6.5, followed by a second addition until reaching the predetermined pH.

It is preferable that temperature at the end of the precipitation be maintained at values below 60° C. for process yield optimisation.

Preferably, temperature is maintained at around 50° C.

The 1,1-cyclohexane diacetic acid monoamide thus obtained is transformed into gabapentin by known methods, e.g. by Hoffmann rearrangement, acidification, extraction, purification of an aqueous solution of gabapentin hydrochloride on a strong cationic ionic exchange resin followed by recrystallisation as described in the international patent application WO 02/34709 in the name of the same Applicant.

Therefore, a further object of the present invention is a process for the preparation of gabapentin which comprises the preparation of 1,1-cyclohexane diacetic acid monoamide by basic hydrolysis of α,α'-diaminocarbonyl-β,β-pentamethylene glutarimide.

The process object of the present invention allows to obtain 1,1-cyclohexane diacetic acid monoamide directly from the dinitryl intermediate, avoiding isolation of 1,1-cyclohexane diacetic acid.

The known preparation steps, which entail the conversion of the acid to monoamide via anhydride, are thereby eliminated.

The process object of the present invention allows to obtain the 1,1-cyclohexane diacetic acid monoamide by fewer synthetic steps and, consequently, with reduced time and costs.

By operating according to the method object of the present invention, a product is obtained which has similar characteristics to the one obtained with known methods, pure and suitable for the subsequent steps of gabapentin preparation.

A practical embodiment of the process object of the present invention comprises the preparation of a water/sulphuric acid solution; addition of dinitryl in portions so that each portion is added after solubilising the preceding portion; a check of the end of the reaction; neutralization of the solution and the subsequent diamide isolation.

Addition of the diimide at low temperature in a sodium hydroxide solution and heating the suspension thus obtained for a few hours at reflux whilst keeping ammonia release under control; decarboxylation of the diacid formed by adding a solution of water and synthetic hydrochloric acid at a portion of about 15-20% by weight of the diacid solution maintained at a temperature around 50° C. and heating the reaction mixture to about 95° C.; addition of the remaining diacid solution maintaining temperature around 95° C. until the reaction is completed; hydrolysis of the imide by adding sodium hydroxide, bringing subsequently to reflux and the product precipitation by acidification.

For better illustrating the invention the following examples are now given.

EXAMPLE 1

Synthesis of α,α'-diaminocarbonyl-β,β-pentamethylene glutarimide

A basic reducer was collected to a reactor A, then 16.0 kg of demineralised water were charged and subsequently, maintaining temperature below 60° C., 135.8 kg (74.0 l) of sulphuric acid (96% w/w) were added with a metering pump.

The loading line and the metering pump were washed with 1.6 kg of demineralised water.

The washings were added to the solution already contained in the reactor A.

The sulphuric acid solution was cooled to 25-30° C., then 12.5 kg of dry dinitryl were charged from a hatch.

A suspension was obtained, which was heated to about 60° C.

This temperature was maintained until obtaining a solution in about one hour and 12.5 kg of dry dinitryl were again added.

The suspension thus obtained was brought to about 60° C. and maintained at that temperature until dissolution in about 2 hours.

An additional 12.5 kg of dry dinitryl were then added.

The suspension thus obtained was brought and maintained to about 60° C.

After about four hours, the reaction check was carried out.

If the reaction check was within limits, the mixture was cooled to about 50° C.

In a reactor B, 102.0 kg of demineralised water were charged.

The water was heated to about 40-45° C., then, letting the temperature rise spontaneously to 50-55° C., the diamide solution contained in the reactor A was added in about 2-3 hours through a loading line.

A dense, but suitable for agitation solution was obtained.

In the reactor A were charged 11.1 kg of demineralised water and subsequently letting the temperature rise to 50-55° C., 11.1 kg (6.0 l) of sulphuric acid (96% w/w) were charged with anti-acid pump.

The solution was maintained for about 10 minutes at 50-55° C. and it was then added to the suspension formed in the reactor B through the loading line.

In the reactor A were charged 14.0 kg of demineralised water, which after about 10 minutes at 50-55° C. were added to the suspension present in the reactor B through the loading line.

The suspension in the reactor B was maintained at 50-55° C. for about 30 minutes, then it was cooled to 15-20° C. in about 1.5 hours.

After at least one hour at 15-20° C., several centrifuging operations were carried out, washing the panel multiple times with demineralised water.

Indicatively, a total of 180.0 kg of demineralised water were used for washings in the centrifuge.

The mother liquors were constituted by 50% sulphuric acid and were placed in plastic or metal drums, coated with anti-acid materials.

About 60.5 kg of humid product were obtained which, dried under vacuum at 50° C., yield about 55.5 kg of dry product.

$^1$H NMR (DMSO-d6): δ 1.34-1.88 (m, 10H), 4.00 (s, 2H), 7.20 (s, 2H, $NH_2$) and 7.85 (s, 2H, $NH_2$, 10.94 (s, 1H).

$^{13}$C NMR (DMSO-d6): δ 20.55 (t, 2C), 25.29 (t, 1C), 31.06 (t, 2C), 38.22 (s, 1C), 54.16 (d, 2C), 168.83 (s, 2C), 170.50 (s, 2C).

MS (E.I. mode): m/z 250 (M–$NH_3$), 222 ((M–$NH_3$)—C=O), 122 ((M–$NH_3$)—$NH_2$COCHCONHCO).

I.R. (KBr): 3409, 3188 (NH stretch, 2937-2865 (C—H stretch of CH and $CH_2$), 1735, 1696, 1638 (C=O stretch), 1417, 1391, 1361 (C—H bend of CH and $CH_2$) $cm^{-1}$.

EXAMPLE 2

Synthesis of α, α'-dicarboxy-β,β-pentamethylene glutarimide di-sodium di-salt

In a reactor C, 170.8 kg (128.4 l) of electrolytic soda were charged under intercepted vacuum.

The loading line was washed with 1.5 kg of demineralised water which was loaded in reactor C.

The reactor was vented with nitrogen, an then it was connected to an acid reducer.

The electrolytic soda solution was cooled to about 0° C., then 90.0 kg of dry diamide were charged from the hatch.

The suspension was heated in about one hour to 55° C. and it was maintained at temperature until the solid was completely dissolved (about 10 minutes), then the solution was brought to about 105° C. in about four hours. The solution was maintained at temperature for about half an hour, then it was cooled to about 50° C.

EXAMPLE 3

Synthesis of pentamethylene glutarimide

The solution obtained as described in the previous example was transferred at 50° C. in a reactor D, then after weighing the solution about 37.9 kg (about 28.5 l) of solution of diacid sodium salt, corresponding to a portion of about 15% by weight of the reaction mixture, were charged in reactor C, whilst the rest of the solution was maintained at 50° C. in reactor D.

In reactor C were charged 70 kg of demineralised water letting temperature drop spontaucously, and subsequently 2.8 kg (2.4 l) of synthetic hydrochloric acid were charged by means of an anti-acid pump.

The loading line and the anti-acid pump were washed with 11.5 kg of demineralised water and the washings were added to the solution contained in reactor C.

The temperature inside reactor A was brought to about 95° C. and it was maintained until the transformation from diacid sodium salt solution to imide suspension.

Maintaining the temperature at about 95° C., about 215 kg (about 161.5 l) of diacid sodium salt solution, i.e. all of the solution left in reactor D, were charged in reactor C in about one hour.

Reactor D and the loading line were washed with 12.0 kg of demineralised water.

The washing was added to the reaction in reactor C.

Temperature was maintained for about two hours, whereupon the suspension was cooled to about 80° C.

EXAMPLE 4

Synthesis of 1,1-cyclohexane diacetic acid monoamide 25.7 kg (19.3 l) of electrolytic soda were charged in reactor C by means of metering pump.

The temperature was brought to about 95° C. and it was maintained until the complete dissolution of the solid, then the mixture was brought to reflux (101-105° C.).

Reflux was maintained for about six hours, then the reaction check was carried out At the completion of the reaction, the solution was cooled to about 20° C. with precipitation of a solid white flocculate, then, at temperature 45.0 kg (57.3) of isopropanol were charged and subsequently in about one hour, maintaining temperature below 25° C., about 125 kg (107.7 l) of synthetic hydrochloric acid were charged until reaching a pH of 6.5±0.2, measured with pH meter.

Once the desired pH was reached, the suspension was heated to 35-40° C. and it was maintained at this temperature until dissolution of the solid.

At the completion of the dissolution, the solution was transferred into reactor E and subsequently 20 kg of demineralised water were charged in the reactor.

The washing was kept under stirring for 5-10 minutes, then it was transferred into reactor E.

The internal temperature of reactor E was regulated to about 35-40° C. then, maintaining temperature, 40 kg (34.5 l) of synthetic hydrochloric acid were added in about one hour until reaching a pH of 4.0-4.5, measured with paper.

The pH of the suspension was checked to be stable for at least 10-15 minutes, then the internal temperature of reactor E was brought to about 50° C. and it was maintained for about 30 minutes.

In about one and one half hours the suspension was cooled to about 15-20° C. and after about one hour several centrifuging operations were carried out. The panel was washed twice with a mixture formed by isopropanol and water.

In total, 23.6 kg (30 k) of isopropanol and 30 kg of demineralised water were used. After one washing with the alcoholic mixture, the panel was subjected to six washings with water.

In total, 270 kg of demineralised water were indicatively used.

78.0 kg of humid product were obtained, which after drying at about 50° C. under vacuum yield about 59.0 kg of the desired dry product.

EXAMPLE 5

Synthesis of 1-(aminomethyl)-cyclohexane acetic acid

The 1,1-cyclohexane diacetic acid monoamide thus obtained is transformed into gabapentin by known methods, e.g. by Hoffmann rearrangement, acidification, extraction, purification of an aqueous solution of gabapentin hydrochloride on a strong cationic ionic exchange resin followed by recrystallisation as described in the international patent application WO 02/34709 in the name of the same Applicant.

The invention claimed is:

1. A process for the preparation of 1,1-cyclohexane diacetic acid monoamide, the process comprising:
   a) hydrolysis of α,α'-diaminocarbonyl-β,β-pentamethylene glutarimide, thereby obtaining α,α'-di-acid disodium salt;
   b) decarboxylation of the product obtained in a), thereby obtaining pentamethylene-glutarimide; and
   c) hydrolysis of pentamethylene-glutarimide and precipitation of the product obtained in c).

2. The process according to claim 1, wherein the basic hydrolysis reaction is carried out by reaction with a sodium hydroxide solution.

3. The process according to claim 1, wherein a) is carried out by addition of α,α'-diaminocarbonyl-β,β-pentamethylene glutarimide to a sodium hydroxide solution and bringing to reflux.

4. The process according to claim 3, wherein the sodium hydroxide solution has a concentration around 30%.

5. The process according to claim 3, wherein the addition of α,α'-diaminocarbonyl-β, β-pentamethylene glutarimide is carried out at a temperature from −5° C. to 5° C.

6. The process according to claim 3, wherein a molar ratio of sodium hydroxide to α,α'-diaminocarbonyl-β,β-pentamethylene glutarimide is from 3.5 to 4.

7. The process according to claim 1, wherein b) is carried out by addition of a solution of hydrochloric acid at a portion of the solution obtained from a), heating, formation of a suspension and addition of the remaining solution obtained from a).

8. The process according to claim 7, wherein the heating of the reaction mixture takes place until a temperature of about 95° C. is reached.

9. The process according to claim 1, wherein c) is carried out by addition of a sodium hydroxide solution, bringing to reflux and precipitating the resultant product by addition of hydrochloric acid.

10. The process according to claim 9, wherein the sodium hydroxide solution has a concentration comprised from 10 to 30%.

11. The process according to claim 9, wherein a molar ratio of sodium hydroxide to α,α'-diaminocarbonyl-β,β-pentamethylene glutarimide is from 3.8 to 4.7.

12. The process according to claim 9, wherein a molar ratio of sodium hydroxide to α,α'-diaminocarbonyl-β,β-pentamethylene glutarimide about 4.3.

13. The process according to claim 9, wherein the product precipitation is carried out in the presence of a precipitation co-solvent.

14. The process according to claim 13, wherein the precipitation co-solvent is isopropanol.

15. The process according to claim 1 further comprising the preparation of α,α'-diaminocarbonyl-β,β-pentamethylene glutarimide by hydrolysis of α,α'-dicyan-β,β-pentamethylene glutarimide with a solution of sulphuric acid.

16. The process according to claim 15, wherein the hydrolysis reaction is carried out at a temperature from 25 and 70° C.

17. The process according to claim 1, wherein α,α'-diaminocarbonyl-β,β-pentamethylene glutarimide is in solid form.

18. The process according to claim 1, wherein α,α'-diaminocarbonyl-β,β-pentamethylene glutarimide is in solid form with a purity higher than 95%.

19. A process for the preparation of gabapentin, the process comprising:
   a) hydrolysis of α,α'-diaminocarbonyl-β,β-pentamethylene glutarimide, thereby obtaining α,α'-di-acid disodium salt;
   b) decarboxylation of the product obtained in a), thereby obtaining pentamethylene-glutarimide;
   c) hydrolysis of pentamethylene-glutarimide and precipitation of the product obtained in c); and
   d) transforming the obtained 1,1-cyclohexane diacetic acid monoamide to gabapentin by a process comprising Hoffmann rearrangement, acidification, extraction, and purification.

* * * * *